United States Patent [19]

Keck et al.

[11] 4,073,942

[45] Feb. 14, 1978

[54] HALO-SUBSTITUTED HYDROXYBENZYL-AMINES AS SECRETOLYTIC AGENTS

[75] Inventors: Johannes Keck; Sigfrid Püschmann; Gerd Krüger, all of Biberach an der Riss; Klaus-Reinhold Noll, Warthausen-Oberhofen; Matyas Leitold, Biberach an der Riss; Helmut Pieper, Mettenberg, all of Germany

[73] Assignee: Boehringer Ingelheim GmbH, Ingelheim am Rhein, Germany

[21] Appl. No.: 635,220

[22] Filed: Nov. 25, 1975

Related U.S. Application Data

[63] Continuation-in-part of Ser. No. 408,071, Oct. 19, 1973, abandoned, and Ser. No. 561,223, March 24, 1975, abandoned.

[30] Foreign Application Priority Data

| Oct. 23, 1972 | Germany | 2251891 |
| Apr. 26, 1973 | Germany | 2320967 |
| Sept. 17, 1973 | Germany | 2346743 |
| Apr. 3, 1974 | Germany | 2416143 |

[51] Int. Cl.$^2$ .................. A61K 31/135; C07C 87/29
[52] U.S. Cl. .................................. 424/330; 260/570.9
[58] Field of Search ...................... 424/330; 260/570.9

[56] References Cited

U.S. PATENT DOCUMENTS

| 3,399,226 | 8/1968 | Saari | 260/570.9 |
| 3,406,024 | 10/1968 | Richter et al. | 260/570.9 |
| 3,457,354 | 7/1969 | Stone | 424/330 |
| 3,536,713 | 10/1970 | Keck et al. | 260/253 |
| 3,781,359 | 12/1973 | Randall et al. | 260/570.9 |
| 3,794,734 | 2/1974 | Cragoe, Jr. | 424/330 |
| 3,809,721 | 5/1974 | Schultz et al. | 260/570.9 |

OTHER PUBLICATIONS

Cronenberger et al – Chimie Therapeutique, Mar.-Apr. 1968, No. 2, pp. 87–99.

*Primary Examiner*—Frederick E. Waddell
*Attorney, Agent, or Firm*—Hammond & Littell

[57] ABSTRACT

Compounds of the formula

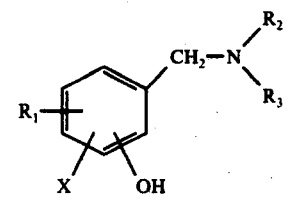

wherein
 X is chlorine or bromine;
 $R_1$ is hydrogen, chlorine or bromine;
 $R_2$ is isopropyl; tert.butyl; tert.pentyl; mono-, di- or tri-hydroxy-substituted branched alkyl of 3 to 5 carbon atoms; cyclohexyl; or hydroxycyclohexyl; and
 $R_3$ is alkyl of 1 to 4 carbon atoms or, when $R_2$ is other than cyclohexyl, also hydrogen;

and non-toxic, pharmacologically acceptable acid addition salts thereof; the compounds as well as their salts are useful as secretolytics, antitussives, anti-ulcerogenics and stimulants for the production of the surfactant or anti-atelectasis factor of the alveoli.

2 Claims, No Drawings

HALO-SUBSTITUTED HYDROXYBENZYL-AMINES AS SECRETOLYTIC AGENTS

This is a continuation-in-part of copending applications Ser. No. 408,071 filed Oct. 19, 1973, and Ser. No. 561,223 filed Mar. 24, 1975, both now abandoned.

This invention relates to novel halo-substituted hydroxybenzylamines and acid addition salts thereof, as well as to various methods of preparing these compounds.

More particularly, the present invention relates to a novel class of compounds represented by the formula

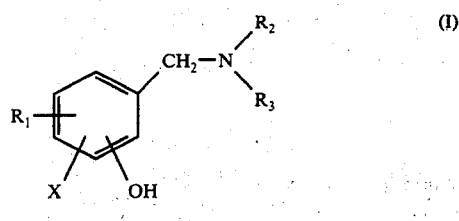

wherein
X is chlorine or bromine;
$R_1$ is hydrogen, chlorine or bromine;
$R_2$ is isopropyl; tert.butyl; tert.pentyl; mono-, di- or tri-hydroxy-substituted branched alkyl of 3 to 5 carbon atoms; cyclohexyl; or hydroxycyclohexyl; and
$R_3$ is alkyl of 1 to 4 carbon atoms or, when $R_2$ is other than cyclohexyl, also hydrogen;
and non-toxic, pharmacologically acceptable acid addition salts thereof.

The compounds embraced by formula I may be prepared by various methods involving known chemical principles, among which the following have proved to be particularly convenient and efficient:

Method A

By reaction of a compound of the formula

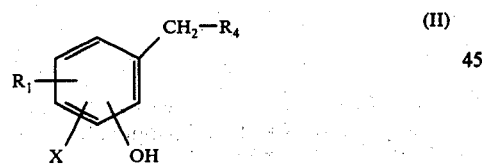

wherein $R_1$ and X have the same meanings as in formula I and $R_4$ is hydroxyl, chlorine, bromine, iodine, acyloxy, sulfonyloxy, alkoxy, aryloxy or aralkoxy,
with an amine of the formula

wherein $R_2$ and $R_3$ have the same meanings as in formula I.

The reaction is appropriately performed in a solvent, such as acetone, carbon tetrachloride, chloroform, ethanol, tetrahydrofuran, benzene, toluene, dioxane or tetrahydronaphthalene, or in an excess of the amine reactant of the formula III and, depending on the reactivity of $R_4$, at temperatures between $-70°$ and $200°$ C. The reaction may, however, be carried out as well in the absence of a solvent.

If $R_4$ is halogen, the reaction is preferably carried out at temperatures between $0°$ and $150°$ C, for example at the boiling point of the particular solvent which is used, and appropriately in the presence of a hydrogenhalide-binding agent, for instance an inorganic base, such as sodium carbonate or sodium hydroxide, or in the presence of an ion exchanger or a tertiary organic base, such as triethylamine or pyridine. The latter may serve as a solvent at the same time.

If $R_4$ is sulfonyloxy, for instance 4-methyl-phenyl-sulfonyloxy, the reaction is preferably performed at temperatures between $-70°$ and $50°$ C.

If $R_4$ is acyloxy, for example acetoxy, benzoyloxy, alkoxy, aryloxy or aralkoxy, the reaction is optionally carried out in the presence of an acid catalyst, such as ammonium chloride, preferably at temperatures between $0°$ and $200°$ C.

If $R_4$ is hydroxyl, the reaction is optionally performed in the presence of an acid catalyst, such as hydrobromic acid, p-toluene-sulfonic acid or butyric acid, or optionally in the presence of an alkaline catalyst, such as potassium hydroxide or magnesium oxide, preferably at temperatures between $120°$ and $180°$ C. The reaction may, however, be performed as well without any solvent.

Method B

By reaction of an aldehyde of the formula

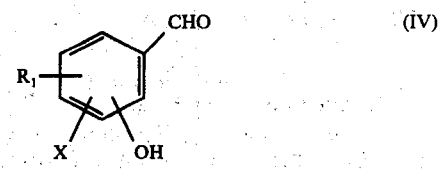

wherein $R_1$ and X have the same meanings as in formula I, with an amine of the formula

wherein $R_2$ and $R_3$ have the same meanings as in formula I, or with the corresponding formamide in the presence of formic acid.

The reductive amination is preferably carried out at temperatures between $50°$ and $250°$ C, optionally in a solvent and optionally while distilling off at the same time the water that is formed. It is of special advantage, however, to use the amine of the formula III and/or the formic acid during the reaction as a solvent at the same time. If $R_3$ is hydrogen in a compound of the formula III, the reaction mixture obtained is refluxed after the reaction with a dilute acid, such as 2 N hydrochloric acid.

Method C

For the preparation of a compound of the formula I wherein $R_3$ is hydrogen:
By reduction of a compound of the formula

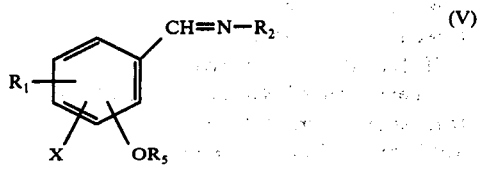

or of a compound of the formula

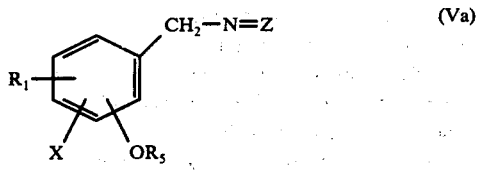

wherein $R_1$, $R_2$ and X have the same meanings as in formula I, Z is cyclohexylidene optionally substituted by hydroxyl or by alkyl of 1 to 4 carbon atoms or branched alkylidene of 3 to 5 carbon atoms, and $R_5$ is hydrogen or organic acyl.

If $R_5$ is hydrogen, the reduction is appropriately carried out with catalytically activated hydrogen, for example, with hydrogen in the presence of Raney nickel or Raney cobalt; or with nascent hydrogen generated, for instance, with activated metallic aluminum and water; or with sodium amalgam and ethanol; or with zinc and hydrochloric acid; or the reduction is carried out with a complex metal hydride — which is of special advantage —, such as lithium aluminum hydride or sodium borohydride, in the presence of an appropriate solvent, such as methanol, ethanol, ethanol/water, tetrahydrofuran, dioxane, dioxane/water, pyridine or ether, at temperatures up to the boiling point of the solvent used, for instance between −50° and 100° C.

If, in a compound of the formula V or Va, $R_5$ is organic acyl, the latter is split off during the reduction with nascent hydrogen or with a complex metal hydride.

Method D

For the preparation of a compound of the formula I wherein $R_3$ is other than hydrogen, and $R_2$ and $R_3$ are not substituted by hydroxyl.

By alkylation of a compound of the formula

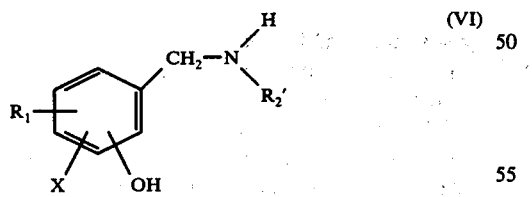

wherein $R_1$ and X have the same meanings as in formula I and $R_2'$ is hydrogen or alkyl of 1 to 4 carbon atoms and has the same meanings as $R_2$ in formula I except branched alkyl of 3 to 5 carbon atoms substituted with 1 to 3 hydroxyls, and hydroxycyclohexyl, with a compound of the formula

wherein $R_3'$ is branched alkyl of 3 to 5 carbon atoms, cyclohexyl, or has the same meanings as $R_3$ in formula I except hydrogen and W is halogen or sulfonyl.

The reaction is advantageously carried out in the presence of a solvent such as methanol, dioxane or dimethylformamide, appropriately at temperatures between −20° and 150° C, preferably, however, at the boiling point of the solvent used.

A methylation may also be carried out with formaldehyde in the presence of formic acid at elevated temperatures, for instance at the boiling point of the reaction mixture.

Method E

By reaction of a phenol of the formula

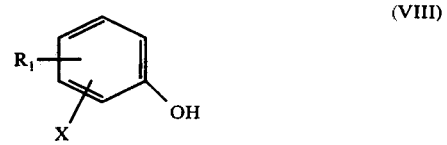

wherein $R_1$ and X have the same meanings as in formula I, the X substituent being in the 2-position of the compound of the formula VIII, with formaldehyde or paraformaldehyde and an amine of the formula

wherein $R_2$ and $R_3$ have the same meanings as in formula I.

The reaction is advantageously carried out in the presence of a solvent such as water, methanol, ethanol or dioxane, at temperatures between 0° and 100° C, preferably, however, at the boiling point of the particular solvent which is used.

The reaction may also be carried out in such a way that a compound of the formula

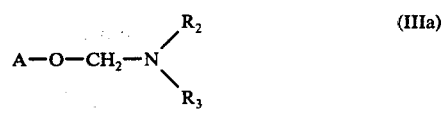

wherein $R_2$ and $R_3$ have the same meanings as in formula I and A is lower alkyl, optionally formed in situ, is reacted with a compound of the formula VIII.

Method F

By halogenation of a compound of the formula

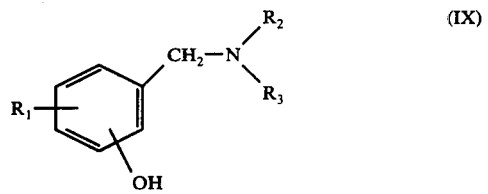

wherein $R_1$, $R_2$ and $R_3$ have the same meanings as in formula I.

The halogenation is performed with a halogenating agent, for example, with chlorine, bromine, iodobenzene dichloride or tribromophenolbromine, preferably in the presence of a solvent, for instance in 50–100% acetic acid, in methylene chloride or in tetrahydrofuran in the presence of a tertiary organic base, and appropriately at temperatures between −20° and 50° C. Per mol of a compound of the formula IX, used as a base or a salt as well, for example, as hydrochloride, appropriately 1 or 2 mols of a halogenating agent or a slight excess are used. If a hydrohalic acid salt is formed during the reaction it may be isolated as such or may, if desired, be further purified via the base.

The compounds of formulas II through IX used as starting materials in Methods A through F are either known from the literature or may be prepared according to processes described in the literature.

The benzyl halides of the formula II, for example, may be prepared from the corresponding toluene derivates by reaction with N-bromo-succinimide, or with halogen under ultra-violet radiation.

A benzyl alcohol derivative of the formula II is obtained, for instance, by reaction of a corresponding benzyl alcohol with a corresponding acid in the presence of hydrochloric acid, or by reaction of a corresponding benzyl halide with a corresponding alcohol in the presence of barium carbonate. A benzyl alcohol of the formula II is prepared by halogenation of a corresponding benzyl alcohol.

The aldehydes of the formula IV are obtained, for example, by halogenation of the corresponding benzaldehydes, and the imines of the formulas V and Va are obtained from the corresponding primary amines and the corresponding carbonyl compounds. By reduction, for example with sodium boron hydride, of a compound of the formulas V or Va thus obtained, a compound of the formula VI is prepared.

The benzylamines of formula IX are prepared, for instance, by reaction of the corresponding benzyl halides with the corresponding amines.

Since the compounds embraced by formula I are bases, they form acid addition salts with inorganic or organic acids, and may, if desired, be converted into such salts by conventional methods. Examples of non-toxic, pharmacologically acceptable acid addition salts are those formed with hydrochloric acid, phosphoric acid, hydrobromic acid, sulfuric acid, lactic acid, tartaric acid, maleic acid, 8-chlorotheophylline or the like.

The following examples illustrate the present invention and will enable others skilled in the art to understand it more completely. It should be understood, however, that the invention is not limited solely to the particular examples given below.

EXAMPLE 1

N-Ethyl-N-cyclohexyl-(3,5-dibromo-2-hydroxy)-benzylamine and its hydrochloride by method A 17 gm of 3,5-dibromo-2-hydroxy-benzylbromide and 12.7 gm of N-ethyl-N-cyclohexylamine were heated for 3 hours while refluxing in 150 ml of ethanol. Subsequently the reaction mixture was evaporated to dryness. The residue was shaken with 150 ml of chloroform and 200 ml of water. The chloroform layer was separated, filtered and evaporated to dryness. The residue was dissolved in ethanol and acidified with ethanolic hydrochloric acid, whereupon N-ethyl-N-cyclohexyl-(3,5-dibromo-2-hydroxy)-benzylamine hydrochloride, m.p. 193°–194° C (decomp.), of the formula

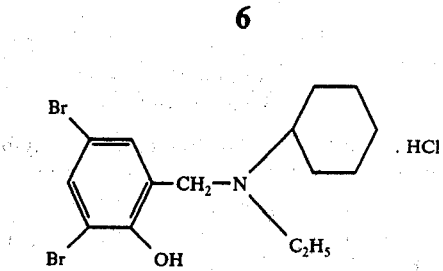

crystallized out.

EXAMPLE 2

N-Methyl-N-cyclohexyl-(3,5-dibromo-2-hydroxy)-benzylamine and its hydrochloride by method B 21 gm of 3,5-dibromo-salicylaldehyde, 56.5 gm of N-methyl-N-cyclohexylamine and 23 gm of formic acid were heated for 6 hours to 70°–80° C. After cooling, the reaction product was shaken with chloroform and dilute ammonia. The chloroform layer was separated and evaporated to dryness. The residue was purified by means of chromatography over 800 gm of silicagel with ethyl acetate/chloroform (1:1). After 0.5 liter of first runnings, the other 0.5 liter was gathered and evaporated to dryness. The residue was dissolved in 50 ml of ethanol and acidified with ethanolic hydrochloric acid. The N-methyl-N-cyclohexyl-(3,5-dibromo-2-hydroxy)-benzylamine hydrochloride, m.p. 189°–181° C (decomp.), of the formula

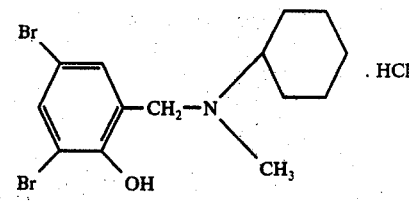

crystallized out.

EXAMPLE 3

N-(Cis-3'-hydroxy-cyclohexyl)-3,5-dibromo-4-hydroxy-benzylamine and its hydrochloride by method C 19 gm of N-(3,5-dibromo-4-hydroxy-benzylidene)-cis-3-amino-cyclohexanol (m.p. 231°–233° C, decomp.) were suspended in 0.5 liter of ethanol and mixed with 2 gm of sodium boron hydride. The mixture was stirred for 1.5 hours at room temperature. Subsequently 200 ml of 2 N sodium hydroxide solution were added to the mixture and the ethanol was distilled off in vacuo. The remaining solution was mixed with ammonium chloride. In doing so a crystalline precipitate was obtained. The latter was sucked off, washed with water, and dissolved in 100 ml of 2 N hydrochloric acid while heating. After a short time N-(cis-3'-hydroxy-cyclohexyl)-3,5-dibromo-4-hydroxy-benzylamine hydrochloride, m.p. 216°–218° C (decomp.), of the formula

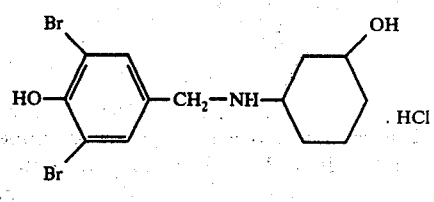

EXAMPLE 4

N-Methyl-N-cyclohexyl-3,5-dibromo-4-hydroxy-benzylamine and its hydrochloride by method D 7.2 gm of N-cyclohexyl-3,5-dibromo-4-hydroxy-benzylamine were dissolved in 20 ml of formic acid and mixed with 2 ml of 40% formaldehyde. The solution was heated for 3 hours over the boiling water bath, subsequently diluted with water and made alkaline with concentrated ammonia. The precipitated base was sucked off, washed with water, and N-methyl-N-cyclohexyl-3,5-dibromo-4-hydroxy-benzylamine hydrochloride, m.p. 168°-170° C (decomp.), of the formula

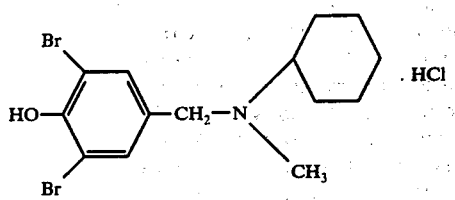

was crystallized from ethanol and ethanolic hydrochloric acid by the addition of a small quantity of ether.

EXAMPLE 5

Using a procedure analogous to that described in Example 1, N-(trans-4'-hydroxy-cyclohexyl)-3,5-dibromo-2-hydroxy-benzylamine and its hydrochloride, m.p. 212°-218° C (decomp.), of the formula

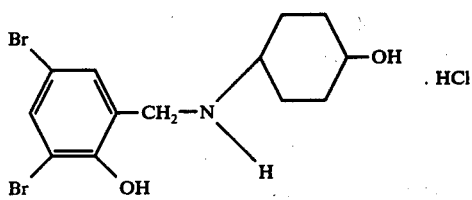

were prepared from 3,5-dibromo-2-hydroxy-benzyl bromide and trans-4-amino-cyclohexanol.

EXAMPLE 6

Using a procedure analogous to that described in Example 1, N-(cis-3'-hydroxy-cyclohexyl)-3,5-dibromo-2-hydroxy-benzylamine and its hydrochloride, m.p. 128°-136° C (decomp.), were prepared from 3,5-dibromo-2-hydroxy-benzyl bromide and cis-3-amino-cyclohexanol.

EXAMPLE 7

Using a procedure analogous to that described in Example 1, N-(trans-3'-hydroxy-cyclohexyl)-3,5-dibromo-2-hydroxy-benzylamine and its hydrochloride, m.p. 203°-204.5° C (decomp.), were prepared from 3,5-dibromo-2-hydroxy-benzyl bromide and trans-3-amino-cyclohexanol.

EXAMPLE 8

Using a procedure analogous to that described in Example 2, N-methyl-N-(trans-4'-hydroxy-cyclohexyl)-3,5-dibromo-2-hydroxy-benzylamine and its hydrochloride, m.p. 120° C (decomp.), were prepared from 3,5-dibromo-salicylaldehyde, trans-4-methyl-amino-cyclohexanol and formic acid.

EXAMPLE 9

Using a procedure analogous to that described in Example 1, N-methyl-N-(cis-3'-hydroxy-cyclohexyl)-3,5-dibromo-2-hydroxy-benzylamine and its hydrochloride, m.p. 80°-83° C (decomp.), were prepared from 3,5-dibromo-2-hydroxy-benzyl bromide and cis-3-methyl-amino-cyclohexanol.

EXAMPLE 10

Using a procedure analogous to that described in Example 1, N-ethyl-N-(trans-4'-hydroxy-cyclohexyl)-3,5-dibromo-2-hydroxy-benzylamine and its hydrochloride, as ethanolate, m.p. 135°-137° C (decomp.), were prepared from 3,5-dibromo-2-hydroxy-benzyl bromide and trans-4-ethylamino-cyclohexanol.

EXAMPLE 11

Using a procedure analogous to that described in Example 1, N-propyl-N-cyclohexyl-3,5-dibromo-2-hydroxy-benzylamine and its hydrochloride, m.p. 178°-180° C (decomp.), were prepared from 3,5-dibromo-2-hydroxy-benzyl bromide and N-propyl-cyclohexylamine.

EXAMPLE 12

Using a procedure analogous to that described in Example 1, N-isopropyl-N-cyclohexyl-3,5-dibromo-2-hydroxybenzylamine, m.p. 108°-110° C, was prepared from 3,5-dibromo-2-hydroxy-benzyl bromide and N-isopropyl-cyclohexylamine.

EXAMPLE 13

Using a procedure analogous to that described in Example 1, N-(trans-4'-hydroxy-cyclohexyl)-3,5-dibromo-4-hydroxy-benzylamine and its hydrochloride, m.p. 220°-225° C (decomp.), of the formula

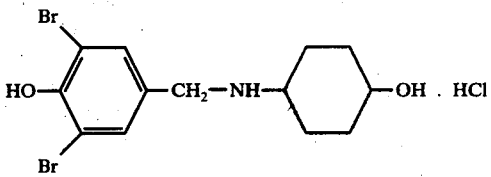

were prepared from 3,5-dibromo-4-hydroxy-benzyl bromide and trans-4-amino-cyclohexanol.

EXAMPLE 14

Using a procedure analogous to that described in Example 1, N-(trans-3'-hydroxy-cyclohexyl)-3,5-dibromo-4-hydroxy-benzylamine and its hydrochloride, m.p. 215°-215.5° C (decomp.), were prepared from 3,5-dibromo-4-hydroxy-benzyl bromide and trans-3-amino-cyclohexanol.

EXAMPLE 15

Using a procedure analogous to that described in Example 1, N-methyl-N-(trans-4'-hydroxy-cyclohexyl)-3,5-dibromo-4-hydroxy-benzylamine and its hydrochloride, m.p. 160°-162° C (decomp.), were prepared from 3,5-dibromo-4-hydroxy-benzyl bromide and trans-4-methylamino-cyclohexanol.

EXAMPLE 16

Using a procedure analogous to that described in Example 1, N-methyl-N-(cis-3'-hydroxy-cyclohexyl)-3,5-dibromo-4-hydroxy-benzylamine, m.p. 133°–136° C, was prepared from 3,5-dibromo-4-hydroxy-benzyl bromide and cis-3-methylaminocyclohexanol.

EXAMPLE 17

Using a procedure analogous to that described in Example 1, N-ethyl-N-(trans-4'-hydroxy-cyclohexyl)-3,5-dibromo-4-hydroxy-benzylamine and its hydrochloride, m.p. 176°–178° C (decomp.), were prepared from 3,5-dibromo-4-hydroxy-benzyl bromide and trans-4-ethylamino-cyclohexanol.

EXAMPLE 18

Using a procedure analogous to that described in Example 1, N-ethyl-N-(cis-3'-hydroxy-cyclohexyl)-3,5-dibromo-4-hydroxy-benzylamine, m.p. 134°–136° C (decomp.), was prepared from 3,5-dibromo-4-hydroxy-benzyl bromide and cis-3-ethylamino-cyclohexanol.

EXAMPLE 19

Using a procedure analogous to that described in Example 1, N-propyl-N-cyclohexyl-3,5-dibromo-4-hydroxy-benzylamine, m.p. 115°–116° C (decomp.), was prepared from 3,5-dibromo-4-hydroxy-benzyl bromide and N-propyl-cyclohexylamine.

EXAMPLE 20

Using a procedure analogous to that described in Example 1, N-methyl-N-cyclohexyl-3,5-dichloro-2-hydroxy-benzylamine and its hydrochloride, m.p. 174°–178° C of the formula

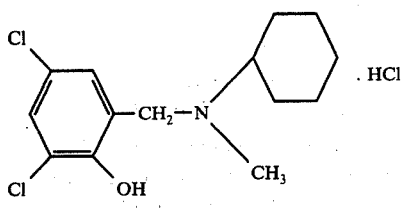

were prepared from 3,5-dichloro-2-hydroxy-benzyl bromide and N-methyl-cyclohexylamine.

EXAMPLE 21

Using a procedure analogous to that described in Example 1, N-ethyl-N-cyclohexyl-3,5-dichloro-2-hydroxy-benzylamine and its hydrochloride, m.p. 185°–188° C (decomp.), were prepared from 3,5-dichloro-2-hydroxy-benzyl bromide and N-ethyl-cyclohexylamine.

EXAMPLE 22

Using a procedure analogous to that described in Example 1, N-ethyl-N-(trans-4'-hydroxy-cyclohexyl)-3,5-dichloro-2-hydroxy-benzylamine and its hydrochloride, m.p. 147°–152° C, of the formula

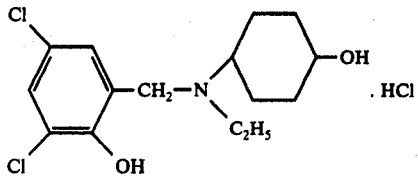

were prepared from 3,5-dichloro-2-hydroxy-benzyl bromide and trans-4-ethylamino-cyclohexanol.

EXAMPLE 23

Using a procedure analogous to that described in Example 1, N-propyl-N-cyclohexyl-3,5-dichloro-2-hydroxy-benzylamine and its hydrochloride, m.p. 168°–170° C were prepared from 3,5-dichloro-2-hydroxy-benzyl bromide and N-propylcyclohexylamine.

EXAMPLE 24

Using a procedure analogous to that described in Example 1, N-isopropyl-N-cyclohexyl-3,5-dichloro-2-hydroxy-benzylamine, m.p. 86°–89° C, was prepared from 3,5-dichloro-2-hydroxy-benzyl bromide and N-isopropyl-cyclohexylamine.

EXAMPLE 25

Using a procedure analogous to that described in Example 1, N-ethyl-N-cyclohexyl-3,5-dichloro-4-hydroxy-benzylamine and its hydrochloride, m.p. 190°–191° C (decomp.), of the formula

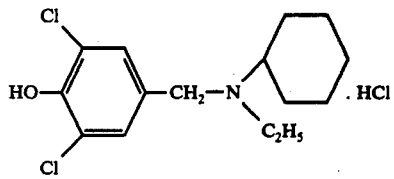

were prepared from 3,5-dichloro-4-hydroxy-benzyl bromide and N-ethyl-cyclohexylamine.

EXAMPLE 26

Using a procedure analogous to that described in Example 1, N-ethyl-N-cyclohexyl-3-bromo-5-chloro-2-hydroxy-benzylamine and its hydrochloride, m.p. 194°–197° C (decomp.), of the formula

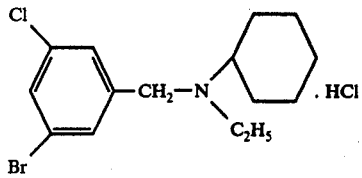

were prepared from 3-bromo-5-chloro-2-hydroxy-benzyl bromide and N-ethyl-cyclohexylamine.

EXAMPLE 27

Using a procedure analogous to that described in Example 1, N-ethyl-N-cyclohexyl-5-bromo-3-chloro-2-hydroxy-benzylamine and its hydrochloride, m.p. 188°–191° C (decomp.), were prepared from 5-bromo-3-chloro-2-hydroxy-benzyl bromide and N-ethyl-cyclohexylamine.

EXAMPLE 28

Using a procedure analogous to that described in Example 2, N-methyl-N-cyclohexyl-(5-bromo-2-hydroxy)-benzylamine and its hydrochloride, m.p. 194°-197° C, of the formula

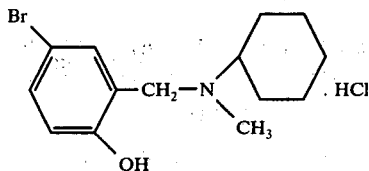

were prepared from 5-bromo-salicylaldehyde, N-methyl-cyclohexylamine and formic acid.

EXAMPLE 29

Using a procedure analogous to that described in Example 2, N-ethyl-N-cyclohexyl-(5-bromo-2-hydroxy)-benzylamine and its hydrochloride, m.p. 175°-178° C, were prepared from 5-bromo-salicylaldehyde, N-ethyl-cyclohexylamine and formic acid.

EXAMPLE 30

Using a procedure analogous to that described in Example 2, N-ethyl-N-(trans-4'-hydroxy-cyclohexyl)-5-bromo-2-hydroxy-benzylamine and its hydrochloride, m.p. 190°-193° C (decomp.), of the formula

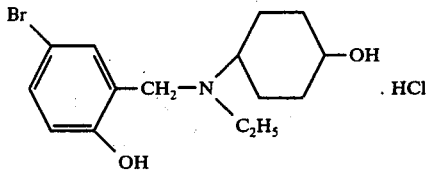

were prepared from 5-bromo-salicylaldehyde, trans-4-ethylaminocyclohexanol and formic acid.

EXAMPLE 31

Using a procedure analogous to that described in Example 2, N-propyl-N-cyclohexyl-5-bromo-2-hydroxy-benzylamine and its hydrochloride, m.p. 166°-169° C (decomp.), were prepared from 5-bromo-salicylaldehyde, N-propyl-cyclohexylamine and formic acid.

EXAMPLE 32

Using a procedure analogous to that described in Example 2, N-isopropyl-N-cyclohexyl-5-bromo-2-hydroxy-benzylamine, m.p. 90°-93° C, was prepared from 5-bromo-salicylaldehyde, N-isopropyl-cyclohexylamine and formic acid.

EXAMPLE 33

Using a procedure analogous to that described in Example 2, N-methyl-N-cyclohexyl-5-chloro-2-hydroxy-benzylamine and its hydrochloride, m.p. 194°-198° C, were prepared from 5-chloro-salicylaldehyde, N-methyl-cyclohexylamine and formic acid.

EXAMPLE 34

Using a procedure analogous to that described in Example 2, N-ethyl-N-cyclohexyl-5-chloro-2-hydroxy-benzylamine and its hydrochloride, m.p. 169°-171° C, were prepared from 5-chloro-salicylaldehyde, N-ethyl-cyclohexylamine and formic acid.

EXAMPLE 35

Using a procedure analogous to that described in Example 2, N-propyl-N-cyclohexyl-5-chloro-2-hydroxy-benzylamine and its hydrochloride, m.p. 140°-142° C, were prepared from 5-chloro-salicylaldehyde, N-propyl-cyclohexylamine and formic acid.

EXAMPLE 36

Using a procedure analogous to that described in Example 2, N-isopropyl-N-cyclohexyl-5-chloro-2-hydroxy-benzylamine, m.p. 85°-88° C, was prepared from 5-chloro-salicylaldehyde, N-isopropyl-cyclohexylamine and formic acid.

EXAMPLE 37

Using a procedure analogous to that described in Example 1, N-methyl-N-cyclohexyl-3-bromo-4-hydroxy-benzylamine and its hydrochloride, m.p. 165°-169° C (decomp.), of the formula

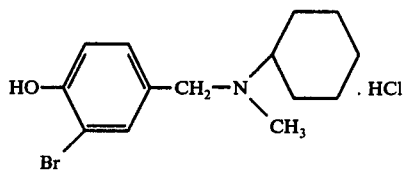

were prepared from 3-bromo-4-hydroxy-benzyl bromide and N-methyl-cyclohexylamine.

EXAMPLE 38

Using a procedure analogous to that described in Example 1, N-ethyl-N-cyclohexyl-3,5-dibromo-4-hydroxy-benzylamine and its hydrochloride, m.p. 180°-181° C (decomp.), were prepared from 3,5-dibromo-4-hydroxy-benzyl bromide and N-ethyl-cyclohexylamine.

EXAMPLE 39

N-Ethyl-N-cyclohexyl-2-bromo-5-hydroxy-benzylamine and its hydrochloride by method A 54 gm of 2-bromo-5-hydroxy-benzyl bromide in 800 ml of carbontetrachloride were mixed with 51 gm of N-ethylcyclohexylamine and refluxed for 1 hour. Subsequently, the reaction mixture was extracted twice with water, and the organic phase was dried with sodium sulfate and evaporated. The residue was purified by means of column chromatography over silicagel with ethyl acetate as the eluant. The crude base was dissolved in ethyl acetate and acidified with absolute ethanolic hydrochloric acid, whereupon N-ethyl-N-cyclohexyl-2-bromo-5-hydroxy-benzylamine hydrochloride, m.p. 183°-188° C (decomp.), of the formula

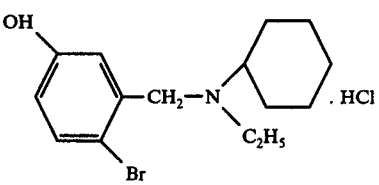

crystallized out.

EXAMPLE 40

N-(Trans-4'-hydroxy-cyclohexyl)-2,4-dibromo-5-hydroxy-benzylamine and its hydrochloride by method C 3.5 gm of N-(2,4-dibromo-5-hydroxy-benzylidene)-trans-4-amino-cyclohexanol in 70 ml of ethanol were mixed dropwise with a solution of 0.4 gm of sodium borohydride in 5 ml of water while stirring. After stirring for 1 hour, 10 ml of 2 N sodium hydroxide solution and 30 ml of water were added to the solution, which was then evaporated to half its volume. Subsequently, the solution was admixed with a saturated aqueous solution of ammonium chloride, thus precipitating N-(trans-4'-hydroxy-cyclohexyl)-2,4-dibromo-5-hydroxy-benzylamine. The precipitate was sucked off, suspended in acetone, warmed and acidified with absolute ethanolic hydrochloric acid, whereupon the base dissolved and the hydrochloride, m.p. 268°-270° C (decomp.), of the formula

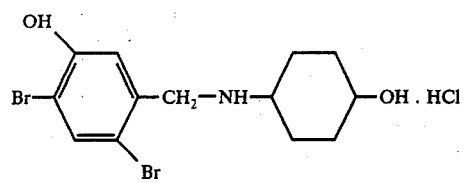

crystallized out immediately.

EXAMPLE 41

N-Methyl-N-cyclohexyl-3-bromo-5-chloro-4-hydroxy-benzylamine by method F 3.6 gm of N-methyl-N-cyclohexyl-3-bromo-4-hydroxy-benzylamine hydrochloride were dissolved in 50 ml of 90% acetic acid and admixed with a solution of 0.75 gm of chlorine in 15 ml of glacial acetic acid while cooling with ice water. After stirring for a short time, the solution was poured into a mixture of ice and 10 N sodium hydroxide solution and extracted three times with methylene chloride. The organic phase was evaporated to dryness. The residue was purified by means of column chromatography over silicagel with ethyl acetate as the eluant, yielding N-methyl-N-cyclohexyl-3-bromo-5-chloro-4-hydroxy-benzylamine, m.p. 136°-138° C, of the formula

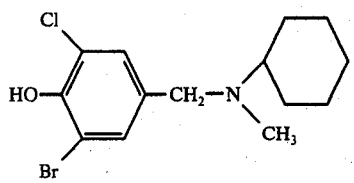

after recrystallization from ethanol/ether.

EXAMPLE 42

N-Ethyl-N-cyclohexyl-5-bromo-3-chloro-4-hydroxy-benzylamine and its hydrochloride by method F 2.3 gm of N-ethyl-N-cyclohexyl-3-chloro-4-hydroxy-benzylamine were dissolved in 20 ml of 75% acetic acid and admixed dropwise, while stirring, with 1.6 gm of bromine. The solution was diluted with water, made alkaline with aqueous concentrated ammonia, and extracted twice with chloroform. The organic phase was dried over sodium sulfate and evaporated. The residue was dissolved in absolute ethanol and acidified with absolute ethanolic hydrochloric acid. Upon addition of ether, N-ethyl-N-cyclohexyl-5-bromo-3-chloro-4-hydroxy-benzylamine hydrochloride, m.p. 165°-168° C (decomp.), of the formula

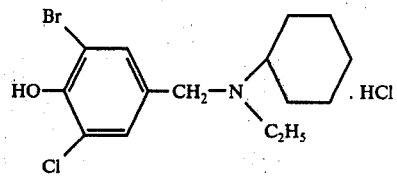

crystallized out.

EXAMPLE 43

N-Ethyl-N-cyclohexyl-3-chloro-2-hydroxy-benzylamine and its hydrochloride by method E 13 gm of N-ethyl-cyclohexylamine and 3 gm of paraformaldehyde were dissolved, while heating, in 100 ml of ethanol, then cooled, admixed with 13 gm of 2-chloro-phenol, left standing for 1.5 hours at room temperature and finally refluxed for 3 hours. Subsequently, the solution was evaporated, and the residue was purified with ethyl acetate on a column of silicagel. The crude base was dissolved in absolute ethanol and acidified with absolute ethanolic hydrochloric acid. N-ethyl-N-cyclohexyl-3-chloro-2-hydroxy-benzylamine hydrochloride, m.p. 177°-178° C (decomp.), of the formula

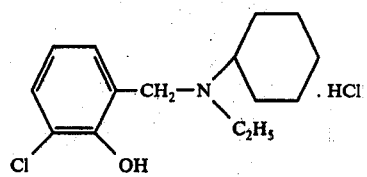

crystallized out when ethyl acetate was added.

EXAMPLE 44

Using a procedure analogous to that described in Example 40, N-(trans-4'-hydroxy-cyclohexyl)-3,5-dichloro-2-hydroxy-benzylamine and its hydrochloride, m.p. 216°-222° C (decomp.), were prepared by reduction of N-(3,5-dichloro-2-hydroxy-benzylidene)-trans-4'-amino-cyclohexanol with sodium borohydride.

EXAMPLE 45

Using a procedure analogous to that described in Example 40, N-(trans-4'-hydroxy-cyclohexyl)-3,5-dichloro-4-hydroxy-benzylamine and its hydrochloride, m.p. 222°-225° C (decomp.), were prepared by reduction of N-(3,5-dichloro-4-hydroxy-benzylidene)-trans-4'-amino-cyclohexanol with sodium borohydride.

EXAMPLE 46

Using a procedure analogous to that described in Example 40, N-(trans-4'-hydroxy-cyclohexyl)-3-bromo-5-chloro-2-hydroxy-benzylamine and its hydrochloride, m.p. 214°-221° C (decomp.), were prepared by reduction of N-(3-bromo-5-chloro-2-hydroxy-benzylidene)-trans-4'-amino-cyclohexanol with sodium borohydride.

EXAMPLE 47

Using a procedure analogous to that described in Example 40, N-(trans-4'-hydroxy-cyclohexyl)-5-bromo-3-chloro-2-hydroxy-benzylamine and its hydrochloride, m.p. 193°–197° C (decomp.), were prepared by reduction of N-(5-bromo-3-chloro-2-hydroxy-benzylidene)-trans-4'-amino-cyclohexanol with sodium borohydride.

EXAMPLE 48

Using a procedure analogous to that described in Example 40, N-(trans-4'-hydroxy-cyclohexyl)-5-bromo-3-chloro-4-hydroxy-benzylamine and its hydrochloride, m.p. 220°–226° C (decomp.), were prepared by reduction of N-(5-bromo-3-chloro-4-hydroxy-benzylidene)-trans-4'-amino-cyclohexanol with sodium borohydride.

EXAMPLE 49

Using a procedure analogous to that described in Example 40, N-(trans-4'-hydroxy-cyclohexyl)-5-bromo-2-hydroxy-benzylamine and its hydrochloride, m.p. 222°–230° C (decomp.), were prepared by reduction of N-(5-bromo-2-hydroxy-benzylidene)-trans-4'-amino-cyclohexanol with sodium borohydride.

EXAMPLE 50

Using a procedure analogous to that described in Example 39, N-(trans-4'-hydroxy-cyclohexyl)-2-bromo-5-hydroxy-benzylamine and its hydrochloride, m.p. 220°–225° C (decomp.), were prepared from 2-bromo-5-hydroxy-benzyl bromide and trans-4'-amino-cyclohexanol.

EXAMPLE 51

Using a procedure analogous to that described in Example 40, N-(trans-4'-hydroxy-cyclohexyl)-3-bromo-4-hydroxy-benzylamine and its hydrochloride, m.p. 225°–227° C (decomp.), were prepared by reduction of N-(3-bromo-4-hydroxy-benzylidene)-trans-4'-amino-cyclohexanol with sodium borohydride.

EXAMPLE 52

Using a procedure analogous to that described in Example 40, N-(trans-4'-hydroxy-cyclohexyl)-3-bromo-2-hydroxy-benzylamine and its hydrochloride, m.p. 194°–196° C (decomp.), were prepared by reduction of N-(3-bromo-2-hydroxy-benzylidene)-trans-4'-amino-cyclohexanol with sodium borohydride.

EXAMPLE 53

Using a procedure analogous to that described in Example 40, N-(trans-4'-hydroxy-cyclohexyl)-2,6-dibromo-3-hydroxy-benzylamine and its hydrochloride, m.p. 269°–271° C (decomp.), were prepared by reduction of N-(2,6-dibromo-3-hydroxy-benzylidene)-trans-4'-amino-cyclohexanol.

EXAMPLE 54

Using a procedure analogous to that described in Example 40, N-(cis-3'-hydroxy-cyclohexyl)-3,5-dichloro-2-hydroxy-benzylamine and its hydrochloride, m.p. 209°–214° C (decomp.), were prepared by reduction of N-(3,5-dichloro-2-hydroxy-benzylidene)-cis-3'-amino-cyclohexanol.

EXAMPLE 55

Using a procedure analogous to that described in Example 40, N-(cis-3'-hydroxy-cyclohexyl)-3,5-dichloro-4-hydroxy-benzylamine and its hydrochloride, m.p. 219°–224° C (decomp.), were prepared by reduction of N-(3,5-dichloro-4-hydroxy-benzylidene)-cis-3'-amino-cyclohexanol.

EXAMPLE 56

Using a procedure analogous to that described in Example 40, N-(cis-3'-hydroxy-cyclohexyl)-3-bromo-5-chloro-2-hydroxy-benzylamine and its hydrochloride, m.p. 197°–201° C (decomp.), were prepared by reduction of N-(3-bromo-5-chloro-2-hydroxy-benzylidene)-cis-3'-amino-cyclohexanol.

EXAMPLE 57

Using a procedure analogous to that described in Example 40, N-(cis-3'-hydroxy-cyclohexyl)-5-bromo-3-chloro-2-hydroxy-benzylamine and its hydrochloride, m.p. 219°–222° C (decomp.), were prepared by reduction of N-(5-bromo-3-chloro-2-hydroxy-benzylidene)-cis-3'-amino-cyclohexanol.

EXAMPLE 58

Using a procedure analogous to that described in Example 40, N-(cis-3'-hydroxy-cyclohexyl)-5-bromo-3-chloro-4-hydroxy-benzylamine and its hydrochloride, m.p. 216°–218° C (decomp.), were prepared by reduction of N-(5-bromo-3-chloro-4-hydroxy-benzylidene)-cis-3'-amino-cyclohexanol.

EXAMPLE 59

Using a procedure analogous to that described in Example 40, N-(cis-3'-hydroxy-cyclohexyl)-5-bromo-2-hydroxy-benzylamine and its hydrochloride, m.p. 148°–151° C (decomp.), were prepared by reduction of N-(5-bromo-2-hydroxy-benzylidene)-cis-3'-amino-cyclohexanol.

EXAMPLE 60

Using a procedure analogous to that described in Example 40, N-(cis-3'-hydroxy-cyclohexyl)-2-bromo-5-hydroxy-benzylamine and its hydrochloride, m.p. 245°–250° C (decomp.), were prepared by reduction of N-(2-bromo-5-hydroxy-benzylidene)-cis-3'-amino-cyclohexanol.

EXAMPLE 61

Using a procedure analogous to that described in Example 40, N-(cis-3'-hydroxy-cyclohexyl)-2,4-dibromo-5-hydroxy-benzylamine and its hydrochloride, m.p. 278°–280° C (decomp.), were prepared by reduction of N-(2,4-dibromo-5-hydroxy-benzylidene)-cis-3'-amino-cyclohexanol.

EXAMPLE 62

Using a procedure analogous to that described in Example 42, N-(cis-3'-hydroxy-cyclohexyl)-3-bromo-4-hydroxy-benzylamine and its hydrochloride, m.p. 214°–220° C (decomp.), were prepared by bromination of 4-hydroxy-N-(cis-3'-hydroxy-cyclohexyl)-benzylamine.

EXAMPLE 63

Using a procedure analogous to that described in Example 40, N-(cis-3'-hydroxy-cyclohexyl)-3-bromo-2-hydroxybenzylamine and its hydrochloride, m.p. 163°–167° C (decomp.), were prepared by reduction of N-(3-bromo-2-hydroxy-benzylidene)-cis-3'-amino-cyclohexanol.

EXAMPLE 64

Using a procedure analogous to that described in Example 40, N-(cis-3'-hydroxy-cyclohexyl)-2,6-dibromo-3-hydroxy-benzylamine and its hydrochloride, m.p. 225°–259° C (decomp.), were prepared by reduction of N-(2,6-dibromo-3-hydroxy-benzylidene)-cis-3'-amino-cyclohexanol.

EXAMPLE 65

Using a procedure analogous to that described in Example 42, N-ethyl-N-cyclohexyl-2-bromo-4-chloro-5-hydroxybenzylamine and its hydrochloride, m.p. 132.5°–137° C (decomp.), were prepared by bromination of N-ethyl-N-cyclohexyl-4-chloro-5-hydroxy-benzylamine.

EXAMPLE 66

Using a procedure analogous to that described in Example 39, N-ethyl-N-cyclohexyl-4-chloro-3-hydroxy-benzylamine and its hydrochloride, m.p. 128°–132° C (decomp.), were prepared from 4-chloro-3-hydroxy-benzyl bromide and N-ethylcyclohexylamine.

EXAMPLE 67

Using a procedure analogous to that described in Example 39, N-ethyl-N-cyclohexyl-2-chloro-5-hydroxy-benzylamine and its hydrochloride, m.p. 210°–211° C, were prepared from 2-chloro-5-hydroxy-benzyl bromide and N-ethyl-cyclohexyl-amine.

EXAMPLE 68

Using a procedure analogous to that described in Example 41, N-ethyl-N-cyclohexyl-2,4-dichloro-5-hydroxy-benzylamine and its hydrochloride, m.p. 179°–186° C (decomp.), were prepared by chlorination of N-ethyl-N-cyclohexyl-5-hydroxybenzylamine.

EXAMPLE 69

Using a procedure analogous to that described in Example 43, N-ethyl-N-cyclohexyl-3-bromo-4-hydroxy-benzylamine and its hydrochloride, m.p. 185°–190° C (decomp.), were prepared from 2-bromo-phenol, paraformaldehyde and N-ethylcyclohexylamine.

EXAMPLE 70

Using a procedure analogous to that described in Example 43, N-ethyl-N-cyclohexyl-4-chloro-2-hydroxy-benzylamine and its hydrochloride, m.p. 144°–146° C, were prepared from 3-chloro-phenol, paraformaldehyde and N-ethyl-cyclohexyl-amine.

EXAMPLE 71

Using a procedure analogous to that described in Example 43, N-ethyl-N-cyclohexyl-3-bromo-2-hydroxy-benzylamine and its hydrochloride, m.p. 171°–173° C, were prepared from 2-bromo-phenol, paraformaldehyde and N-ethyl-cyclohexylamine.

EXAMPLE 72

Using a procedure analogous to that described in Example 43, N-ethyl-N-cyclohexyl-4-bromo-2-hydroxy-benzylamine and its hydrochloride, m.p. 175°–177° C, were prepared from 3-bromo-phenol, paraformaldehyde and N-ethyl-cyclohexylamine.

EXAMPLE 73

Using a procedure analogous to that described in Example 41, N-ethyl-N-cyclohexyl-3-chloro-4-hydroxy-benzylamine and its hydrochloride, m.p. 181°–183° C, were prepared by chlorination of N-ethyl-N-cyclohexyl-4-hydroxy-benzylamine.

EXAMPLE 74

Using a procedure analogous to that described in Example 43, N-ethyl-N-cyclohexyl-2-chloro-4-hydroxy-benzylamine and its hydrochloride, m.p. 165°–166.5° C, were prepared from 3-chloro-phenol, paraformaldehyde and N-ethyl-cyclohexyl-amine.

EXAMPLE 75

Using a procedure analogous to that described in Example 42, N-ethyl-N-cyclohexyl-(2-bromo-4-chloro-3-hydroxy)-benzylamine and its hydrochloride, m.p. 130°–137° C (decomp.), were prepared be bromination of N-ethyl-N-cyclohexyl-4-chloro-3-hydroxy-benzylamine.

EXAMPLE 76

Using a procedure analogous to that described in Example 42, N-ethyl-N-cyclohexyl-2,6-dibromo-3-hydroxy-benzylamine, m.p. 123°–126° C, was prepared by bromination of N-ethyl-N-cyclohexyl-3-hydroxy-benzylamine.

EXAMPLE 77

Using a procedure analogous to that described in Example 41, N-ethyl-N-cyclohexyl-2,4-dichloro-3-hydroxy-benzylamine and its hydrochoride, m.p. 127°–132° C (decomp.), were prepared by chlorination of N-ethyl-N-cyclohexyl-3-hydroxybenzylamine.

EXAMPLE 78

N-(Dihydroxy-tert.butyl)-3,5-dibromo-2-hydroxy-benzylamine and its hydrochloride by method A 21.6 gm of 3,5-dibromo-2-hydroxy-benzyl bromide dissolved in 0.5 liter of carbon tetrachloride were admixed with a solution of 26.4 gm of dihydroxy-tert.butylamine in 100 ml of ethanol and refluxed for 30 minutes. The precipitate formed thereby was sucked off and washed with carbon tetrachloride and water. The crude product was dissolved in absolute ethanol and acidified with ethanolic hydrochloric acid, and N-(dihydroxy-tert.butyl)-3,5-dibromo-2-hydroxy-benzylamine hydrochloride, m.p. 187°–189° C, of the formula

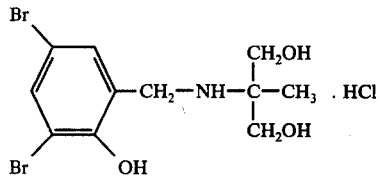

was crystallized out by the addition of ether.

EXAMPLE 79

N-tert.pentyl-3,5-dibromo-2-hydroxy-benzylamine and its hydrochloride by method A 3.5 gm of 3,5-dibromo-2-hydroxy-benzyl alcohol and 1.4 gm of a sodium hydride dispersion (50% in oil) were refluxed for 6 hours in 100 ml of absolute tetrahydrofuran. Subsequently, the reaction mixture was cooled to between −60° and −70° C, and 4.8 gm of p-toluene-sulfonic acid chloride in 50 ml of absolute tetrahydrofuran were added dropwise. Then, it was left standing until a temperature of −30° C was reached and was again cooled to −70° C. 4.4 gm of tert.pentylamine in 50 ml of ether were added dropwise, while stirring, to the reaction mixture until it slowly reached room temperature. Subsequently, it was extracted twice with water, the aqueous layer was extracted with chloroform, and the combined organic phases were evaporated. After purification over a column of silicagel with chloroform-/ethyl acetate (2:1), N-tert.pentyl-3,5-dibromo-2-hydroxy-benzylamine hydrochloride, m.p. 202°–206° C (decomp.), of the formula

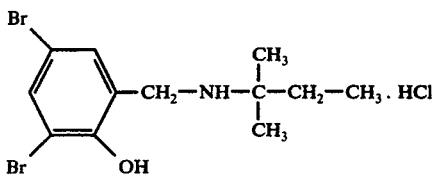

was recrystallized from acetone/ether after having been acidified with ethanolic hydrochloric acid and then recrystallized from water.

EXAMPLE 80

N-Isopropyl-3,5-dibromo-2-hydroxy-benzylamine and its hydrochloride by method C 16 gm of N-isopropylidene-3,5-dibromo-2-hydroxybenzylamine benzylamine in 120 ml of ethanol were admixed with 2 gm of sodium borohydride, stirred for 3 hours, then filtered, admixed with 40 ml of 2 N sodium hydroxide and 200 ml of water, and evaporated to about half its volume. The solution was then admixed with saturated ammonium chloride solution, thus precipitating the crude base. The precipitate was sucked off and washed intensely with water. The product was dissolved in acetone and acidified with ethanolic hydrochloric acid, whereupon N-isopropyl-3,5-dibromo-2-hydroxy-benzylamine hydrochloride, m.p. 195°–199° C (decomp.), of the formula

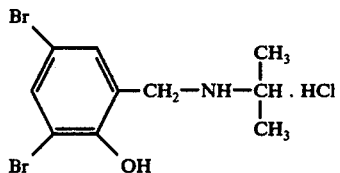

crystallized out immediately.

EXAMPLE 81

Using a procedure analogous to that described in Example 78, N-isopropyl-3,5-dichloro-2-hydroxy-benzylamine and its hydrochloride, m.p. 188°–189.5° C, were prepared from 3,5-dichloro-2-hydroxy-benzyl bromide and isopropylamine.

EXAMPLE 82

Using a procedure analogous to that described in Example 78, N-tert.butyl-3,5-dibromo-4-hydroxy-benzylamine and its hydrochloride, m.p. 234°–236° C (decomp.), of the formula

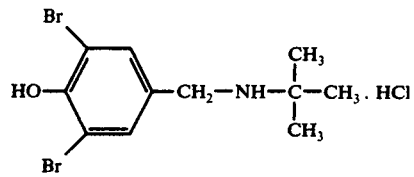

were prepared from 3,5-dibromo-4-hydroxy-benzyl bromide and tert.butylamine.

EXAMPLE 83

Using a procedure analogous to that described in Example 78, N-tert.butyl-3,5-dichloro-2-hydroxy-benzylamine, m.p. 172°–174° C was prepared from 3,5-dichloro-2-hydroxybenzyl bromide and tert.butylamine.

EXAMPLE 84

Using a procedure analogous to that described in Example 78, N-tert.butyl-3,5-dichloro-4-hydroxy-benzylamine and its hydrochloride, m.p. 222°–223° C (decomp.), were prepared from 3,5-dichloro-4-hydroxy-benzyl bromide and tert. butylamine.

EXAMPLE 85

Using a procedure analogous to that described in Example 78, N-tert.pentyl-3,5-dibromo-4-hydroxy-benzylamine and its hydrochloride, m.p. 176°–180° C (decomp.), were prepared from 3,5-dibromo-4-hydroxy-benzyl bromide and tert. pentylamine.

EXAMPLE 86

Using a procedure analogous to that described in Example 78, N-tert.pentyl-3,5-dichloro-4-hydroxy-benzylamine and its hydrochloride, m.p. 203°–207° C (decomp.), were prepared from 3,5-dichloro-4-hydroxy-benzyl bromide and tert. pentylamine.

EXAMPLE 87

Using a procedure analogous to that described in Example, 78, N-(hydroxy-tert.butyl)-3,5-dibromo-2-hydroxybenzylamine and its hydrochloride, m.p. 189°–191° C, were prepared from 3,5-dibromo-2-hydroxy-benzyl bromide and hydroxytert.butylamine.

EXAMPLE 88

Using a procedure analogous to that described in Example 78, N-(hydroxy-tert.butyl)-3,5-dibromo-4-hydroxybenzylamine and its hydrochloride, m.p. 200°–202° C, were prepared from 3,5-dibromo-4-hydroxy-benzyl bromide and hydroxytert.butylamine.

EXAMPLE 89

Using a procedure analogous to that described in Example 78, N-(hydroxy-tert.butyl)-3,5-dichloro-4-hydroxybenzylamine and its hydrochloride, m.p. 208°–212° C (decomp.), were prepared from 3,5-dichloro-4-hydroxy-benzyl bromide and hydroxy-tert.butylamine.

EXAMPLE 90

Using a procedure analogous to that described in Example 78, N-(dihydroxy-tert.butyl)-3,5-dibromo-4-hydroxybenzylamine and its hydrochloride, m.p. 182°–183.5° C, were prepared from 3,5-dibromo-4- hydroxy-benzyl bromide and dihydroxy-tert.butylamine.

EXAMPLE 91

Using a procedure analogous to that described in Example 78, N-(trihydroxy-tert.butyl)-3,5-dibromo-4-hydroxybenzylamine and its hydrochloride, m.p. 189–191.5° C, were prepared from 3,5-dibromo-4-hydroxy-benzyl bromide and trihydroxy-tert.butylamine.

EXAMPLE 92

Using a procedure analogous to that described in Example 78, N-(dihydroxy-tert.butyl)-3,5-dichloro-4-hydroxybenzylamine and its hydrochloride, m.p. 166°–169° C (decomp.), were prepared from 3,5-dichloro-4-hydroxy-benzyl bromide and dihydroxy-tert.butylamine.

EXAMPLE 93

Using a procedure analogous to that described in Example 78, N-(trihydroxy-tert.butyl)-3,5-dibromo-2-hydroxybenzylamine and its hydrochloride, m.p. 185°–187° C (decomp.), were prepared from 3,5-dibromo-2-hydroxy-benzyl bromide and trihydroxy-tert.butylamine.

EXAMPLE 94

Using a procedure analogous to that described in Example 78, N-(trihydroxy-tert.butyl)-3,5-dichloro-4-hydroxy-benzylamine and its hydrochloride, m.p. 170°–174° C (decomp.), were prepared from 3,5-dichloro-4-hydroxy-benzyl bromide and trihydroxy-tert.butylamine.

EXAMPLE 95

N-tert.butyl-3,5-dibromo-2-hydroxy-benzylamine and its hydrochloride by method B 7 gm of 3,5-dibromo-salicylaldehyde, 17.5 gm of tert. butylamine and 7.7 gm of formic acid were heated for 6 hours at 70°–80° C. Subsequently, the reaction mixture was admixed with aqueous 2 N ammonia, vigorously shaken, and the precipitate formed thereby was sucked off. The residue was dissolved in ethanol, acidified with ethanolic hydrochloric acid and admixed with ether in order to crystallize the product out. N-tert.butyl-3,5-dibromo-2-hydroxy-benzylamine hydrochloride, m.p. 216°–220° C (decomp.), was obtained after recrystallization from absolute ethanol/ether.

EXAMPLE 96

N-isopropyl-3,5-dibromo-4-hydroxy-benzylamine and its hydrochloride by method C 7.3 gm of N-(3,5-dibromo-4-hydroxy-benzylidene)-isopropylamine were stirred for 2 hours together with 1 gm of sodium borohydride in 200 ml of ethanol. Some acetone was added to the reaction mixture in order to decompose the excess sodium borohydride; then, it was acidified with 2 N hydrochloric acid and evaporated to a small volume. After addition of 2 N ammonia to alkaline reaction, the yellowish precipitate was sucked off. The residue was dissolved in absolute ethanol and acidified with ethanolic hydrochloric acid. Ether was added to crystallize out N-isopropyl-3,5-dibromo-4-hydroxybenzylamine hydrochloride, m.p. 229°–233° C (decomp.).

EXAMPLE 97

Using a procedure analogous to that described in Example 96, N-isopropyl-3,5-dichloro-4-hydroxy-benzylamine and its hydrochloride, m.p. 223°–231° C (decomp.), were prepared by reduction of N-(3,5-dichloro-4-hydroxy-benzylidene)-isopropylamine.

EXAMPLE 98

Using a procedure analogous to that described in Example 96, N-tert.pentyl-3,5-dichloro-2-hydroxy-benzylamine and its hydrochloride, m.p. 211°–213° C (decomp.), were prepared by reduction of N-(3,5-dichloro-2-hydroxy-benzylidene)-tert.pentylamine.

EXAMPLE 99

Using a procedure analogous to that described in Example 96, N-(hydroxy-tert.butyl)-3,5-dichloro-2-hydroxybenzylamine and its hydrochloride, m.p. 200°–204.5° C (decomp.), were prepared by reduction of N-(3,5-dichloro-2-hydroxy-benzylidene)-hydroxytert.butylamine.

EXAMPLE 100

Using a procedure analogous to that described in Example 96, N-(dihydroxy-tert.butyl)-3,5-dichloro-2-hydroxybenzylamine and its hydrochloride, m.p. 184°–188° C (decomp.), were prepared by reduction of N-(3,5-dichloro-2-hydroxybenzylidene)-dihydroxytert.butylamine.

EXAMPLE 101

Using a procedure analogous to that described in Example 96, N-(trihydroxy-tert.butyl)-3,5-dichloro-2-hydroxybenzylamine and its hydrochloride, m.p. 172°–176° C (decomp.), were prepared by reduction of N-(3,5-dichloro-2-hydroxybenzylidene)-trihydroxytert.butylamine.

EXAMPLE 102

Using a procedure analogous to that described in Example 96, N-tert.butyl-5-bromo-2-hydroxy-benzylamine and its hydrochloride, m.p. 255°–258° C (decomp.), were prepared by reduction of N-(5-bromo-2-hydroxy-benzylidene)-tert.butylamine.

The compounds according to the present invention, that is, those embraced by formula I above and their nontoxic, pharmacologically acceptable acid addition salts, have useful pharmacodynamic properties. More particularly, the compounds of the present invention exhibit a very effective stimulating action on the production of the surfactant or antiatelectasis factor of the alveoli, secretolytic activity, anti-ulcerogenic activity and antitussive activity in warm-blooded animals, such as rats, guinea pigs, cats, rabbits and mice.

The above-indicated pharmacological activities were ascertained for the compounds of the present invention by the methods described below, and the following are the results obtained for a few representative compounds, where A = N-ethyl-N-cyclohexyl-3,5-dibromo-2-hydroxy-benzylamine hydrochloride, B = N-ethyl-N-cyclohexyl-3,5-dibromo-4-hydroxy-benzylamine hydrochloride, C = N-(cis-3'-hydroxy-cyclohexyl)-3,5-dibromo-4-hydroxybenzylamine hydrochloride, D = N-(trans-4'-hydroxy-cyclohexyl)-3-bromo-2-hydroxybenzylamine hydrochloride, E = N-methyl-N-cyclohexyl-3-bromo-5-chloro-4-hydroxy-benzylamine hydrochloride,
F = N-(trans-4'-hydroxy-cyclohexyl)-3,5-dibromo-2-hydroxybenzylamine hydrochloride,
G = N-(dihydroxy-tert.butyl)-3,5-dibromo-2-hydroxy-benzylamine hydrochloride, H = N-(dihydroxy-tert.butyl)-3,5-dichloro-4-hydroxy-benzylamine hydrochloride,
I = N-tert.pentyl-3,5-dibromo-2-hydroxy-benzylamine hydrochloride, and
J = N-methyl-N-cyclohexyl-3,5-dibromo-2-hydroxy-benzylamine hydrochloride.

1. Antitussive Activity 50 mgm/kg of the test compound were administered orally to each animal of a group of 10 awake white rats. These rats were made to cough by a spray of an aqueous solution containing 7.5% citric acid. 30 minutes after the application of the test compound the average change in the number of coughs was determined in percent, compared to a control group of 10 animals [see Engelhorn and Puschmann in Arzneimittelforschung 13, 474–480 (1963)].

TABLE I

| Compound | Average change in the number of coughs, in per cent, 30 minutes after oral application of 50 mgm/kg |
|---|---|
| A | −38 |
| B | −34 |
| C | −35 |

2. Expectorant Effect

The secretolytic activity was tested on 8 to 10 anesthetized rabbits or 5 anesthetized guinea pigs after oral application of 8 mgm/kg of the test compound. The increase of secretion within 2 hours was calculated before and after application of the substance [see Perry and Boyd in Pharmakol. exp. Therap. 73, 65 (1941)].

The circulatory effect in cats was determined under chloralose-urethane narcosis after intravenous application of the test compound (3 animals per dose).

TABLE II

| Compound | Increase of secretion | Circulatory effect in cats |
|---|---|---|
| A | +81% | 4 mgm/kg: no change<br>8 mgm/kg: slight fall of blood-pressure for a short time |
| B | +87% | 8 mgm/kg: no change |

TABLE III

| Compound | Increase of secretion |
|---|---|
| D | +66% |
| E | +65% |
| F | +70% |
| G | +88% |
| H | +88% |
| I | +80% |

3. Anti-ulcerogenic activity

The standard pharmacological test method of K. Tagaki et al, Jap. J. Pharmac. 19, 418 (1969), was used. The abdominal cavity of female rats having a body weight of 220 to 350 gm under ether anesthesia was opened, and the stomach was exposed. Thereafter, 0.05 ml of an aqueous 5% solution of acetic acid was injected in one location between the muscularis mucosae and the submucosa of the stomach of each animal, and the abdominal cavity was closed again. 3 to 5 days after this injection the animals developed stomach ulcers in the mucous membrane at the locus of injection, whereupon the animals were treated over a period of three weeks by adding the test compound at dosage levels of 50 and 100 mgm/kg to their daily food ration, using 5 to 8 animals per dose. The controls received only pulverized rat food. After three weeks, the animals were sacrificed, their stomachs were excised, and the size of the ulcer was determined by measuring its length and width. The anti-ulcerogenic effect of the test compound was expressed in terms of average percent difference in size of the treated ulcers over the controls (100%).

The following table shows the results obtained from these tests:

TABLE IV

| Compound | Dose in mgm/kg p.o. | % Reduction in ulcer size over controls |
|---|---|---|
| Controls | powdered food | 0 |
| J | 50 | −73 |
|  | 100 | −82 |
| F | 50 | −59 |
|  | 100 | −78 |
| A | 50 | −39 |
|  | 100 | −54 |
| C | 50 | −11 |
|  | 100 | −29 |

4. Acute Toxicity

The acute toxicity was determined on groups of 5 white mice after oral application of a dose ranging between 500 mgm/kg and 5000 mgm/kg per animal (time of observation: 72 hours).

TABLE V

| Compound | Acute Toxicity |
|---|---|
| A | >1000 mgm/kg, p.o. (0 of 5 animals dead) |
| B | >1000 mgm/kg, p.o. (0 of 5 animals dead) |
| C | >1000 mgm/kg, p.o. (0 of 5 animals dead) |
| D | > 500 mgm/kg, p.o (0 of 5 animals dead) |
| E | > 500 mgm/kg, p.o. (0 of 5 animals dead) |
| F | >5000 mgm/kg, p.o. (0 of 5 animals dead) |
| G | >5000 mgm/kg, p.o. (0 of 5 animals dead) |
| H | — |
| I | >5000 mgm/kg, p.o. (0 of 5 animals dead) |
| J | >5000 mgm/kg, p.o. (1 of 5 animals dead) |

For pharmaceutical use as secretolytics, antitussives and stimulants of the anti-atelectasis factor, the compounds of the present invention are administered to warm-blooded animals, perorally, parenterally or rectally as active ingredients in customary pharmaceutical compositions, that is, compositions consisting essentially of an inert pharmaceutical carrier and an effective amount of the active ingredient, such as tablets, coated pills, capsules, wafers, powders, solutions, suspensions, emulsions, syrups, suppositories, tinctures, ointments, aerosols and the like. The single effective dose for these purposes is about 0.017 to 0.333 mgm/kg, preferably 0.033 to 0.167 mgm/kg body weight.

For pharmaceutical use as anti-ulcerogenics, the compounds of the formula I or their non-toxic acid addition salts are administered to warm-blooded animals perorally as active ingredients in customary oral dosage unit compositions, that is, compositions in dosage unit form consisting essentially of an inert pharmaceutical carrier and one effective anti-ulcerogenic dosage unit of the active ingredient, such as tablets, coated pills, capsules, wafers, powders, solutions, suspensions, emulsions, syrups and the like. The effective antiulcerogenic oral single dosage unit of the compounds is from 0.42 to 1.67 mgm/kg body weight, preferably 0.5 to 1.0 mgm/kg body weight. The daily dose rate, administered in three to four single doses, is from 1.25 to 6.7 mgm/kg body weight, preferably 1.5 to 4.0 mgm/kg body weight.

The following examples illustrate a few pharmaceutical compositions comprising a compound of the present invention as an active ingredient and represent the best modes contemplated of putting the invention into practical use. The parts are parts by weight unless otherwise specified.

EXAMPLE 103

Syrup

The syrup was compounded from the following ingredients:

| | |
|---|---|
| N-Ethyl-N-cyclohexyl-3,5-dibromo-4-hydroxy-benzylamine hydrochloride | 0.04 parts |
| Tartaric acid | 0.50 parts |
| Benzoic acid | 0.20 parts |
| Ammonium chloride | 0.40 parts |
| Glycerin | 10.00 parts |
| Sorbitol | 50.00 parts |
| Naphthol Red S | 0.01 parts |
| Flavoring | 0.25 parts |
| Ethanol | 10.00 parts |
| Distilled water q.s.ad | 100.00 parts by vol. |

Preparation:

45 gm of the distilled water were warmed to 80° C. Then the tartaric acid, the benzoic acid, the benzylamine, the naphthol and the sorbitol were successively dissolved in the water which was subsequently mixed with the glycerin and an aqueous 20% solution of ammonium chloride. After cooling to room temperature, the ethanol and the flavoring were stirred into the mixture. The syrup was diluted to the indicated volume with distilled water and filtered. Each 10 ml portion of the syrup contained 4 mgm of the benzylamine hydrochloride, and was an oral dosage unit composition with very effective secretolytic and antitussive action, as well as a stimulant effect upon the production of the surfactant or anti-atelectasis factor of the alveoli.

EXAMPLE 104

Drop Solution

The solution was compounded from the following ingredients:

| | |
|---|---|
| N-Ethyl-N-cyclohexyl-3,5-dibromo-4-hydroxy-benzylamine hydrochloride | 0.40 parts |
| p-Hydroxy-benzoic acid methyl ester | 0.07 parts |
| p-Hydroxy-benzoic acid propyl ester | 0.03 parts |
| Polyvinylpyrrolidone | 5.00 parts |
| Anise oil | 0.01 parts |
| Fennel oil | 0.001 parts |
| Ethanol | 10.00 parts |
| Distilled water q.s.ad | 100.00 parts by vol. |

Preparation:

The p-hydroxy-benzoic acid esters, the polyvinylpyrrolidone and the benzylamine salt were successively dissolved in the distilled water warmed to 80° C. The solution was cooled and subsequently mixed with the mixture of the aromatic oils and the ethanol. The solution was diluted to the indicated volume with distilled water and filtered. Each ml of drop solution contained 4 mgm of the benzylamine hydrochloride, and was an oral dosage unit composition with very effective secretolytic and antitussive action, as well as a stimulant effect upon the production of the surfactant or anti-atelectasis factor of the alveoli.

EXAMPLE 105

Tablets

The tablet composition was compounded from the following ingredients:

| | | |
|---|---|---|
| N-Ethyl-N-cyclohexyl-3,5-dibromo-4-hydroxy-benzylamine hydrochloride | | 4.0 parts |
| Lactose | | 60.0 parts |
| Potato starch | | 41.0 parts |
| Polyvinylpyrrolidone | | 4.0 parts |
| Magnesium stearate | | 1.0 parts |
| | Total | 110.0 parts |

Preparation:

The benzylamine salt was admixed with the lactose and the potato starch and granulated through a screen of 1 mm mesh-size with an aqueous 20% solution of the polyvinylpyrrolidone. The moist granulate was dried at 40° C, again passed through the above mentioned screen and admixed with the magnesium stearate. The mixture was compressed into 110 mgm-tablets. Each tablet contained 4 mgm of the benzylamine salt and was an oral dosage unit composition with very effective secretolytic and antitussive action, as well as a stimulant action upon the production of the surfactant or anti-atelectasis factor of the alveoli.

EXAMPLE 106

Coated Pills

The pill core composition was compounded from the following ingredients:

| | | |
|---|---|---|
| N-Ethyl-N-cyclohexyl-3,5-dibromo-4-hydroxy-benzylamine hydrochloride | | 4.0 parts |
| Lactose | | 60.0 parts |
| Potato starch | | 41.0 parts |
| Polyvinylpyrrolidone | | 4.0 parts |
| Magnesium stearate | | 1.0 parts |
| | Total | 110.0 parts |

Preparation:

The benzylamine salt was admixed with the lactose and the potato starch and granulated through a screen of 1 mm mesh-size with an aqueous 20% solution of the polyvinylpyrrolidone. The moist granulate was dried at 40° C, again passed through the above mentioned screen and admixed with the magnesium stearate. The mixture was compressed into 110 mgm-pill cores, which were coated in conventional manner with a thin shell consisting essentially of sugar and talcum, and were then polished with beeswax. Each coated pill contained 4 mgm of the benzylamine salt and was an oral dosage unit composition with very effective secretolytic and antitussive action, as well as a stimulant effect upon the production of the surfactant or anti-atelectasis factor of the alveoli.

EXAMPLE 107

Suppositories

The suppository composition was compounded from the following ingredients:

N-Ethyl-N-cyclohexyl-3,5-dibromo-4-

-continued

| | | |
|---|---:|---|
| hydroxy-benzylamine hydrochloride | 4.0 | parts |
| Suppository base (cocoa butter) | 1696.0 | parts |
| Total | 1700.0 | parts |

Preparation:

The finely pulverized benzylamine salt was stirred into the molten suppository base which had been cooled to 40° C and the mixture was homogenized. The mixture was then poured at about 35° C into cooled suppository molds. Each suppository contained 4 mgm of the benzylamine salt and was a rectal dosage unit composition with very effective secretolytic and antitussive action, as well as a stimulant effect upon the production of the surfactant or anti-atelectasis factor of the alveoli.

EXAMPLE 108

Hypodermic solution

The solution was compounded from the following ingredients:

| | | |
|---|---:|---|
| N-Ethyl-N-cyclohexyl-3,5-dibromo-4-hydroxy-benzylamine hydrochloride | 4.0 | parts |
| Tartaric acid | 2.0 | parts |
| Glucose | 95.0 | parts |
| Distilled water q.s.ad | 2000.0 | parts by vol. |

Preparation:

Some of the distilled water was warmed to 80° C, and the tartaric acid and the benzylamine salt were dissolved therein while stirring. After cooling to room temperature, the glucose was dissolved therein, and the solution was filled into white 2 ml-ampules under aseptic conditions. The filled ampules were then sterilized at 120° C for 20 minutes and sealed. Each ampule contained 4 mgm of the benzylamine salt and was an injectable parenteral dosage unit composition with very effective secretolytic and antitussive action, as well as a stimulant effect upon the production of the surfactant or anti-atelectasis factor of the alveoli.

EXAMPLE 109

Tablets

The tablet composition was compounded from the following ingredients:

| | | |
|---|---:|---|
| N-Cyclohexyl-N-methyl-3,5-dibromo-2-hydroxy-benzylamine hydrochloride | 50.0 | parts |
| Sec. calcium phosphate, anhydrous | 120.0 | parts |
| Colloidal silicic acid | 10.0 | parts |
| Corn starch | 30.0 | parts |
| Polyvinylpyrrolidone | 5.0 | parts |
| Potato starch | 20.0 | parts |
| Maleic acid | 3.0 | parts |
| Magnesium stearate | 2.0 | parts |
| Total | 240.0 | parts |

Preparation:

The benzylamine salt, the calcium phosphate, the colloidal silicic acid and the corn starch are intimately admixed with each other, the mixture is moistened with an ethanolic 10% solution of the polyvinylpyrrolidone containing the maleic acid, the moist mass is granulated through a 1.5 mm-mesh screen, and the granulate is dried at 45° C and again passed through the screen. The granulate is then admixed with the potato starch and the magnesium stearate, and the resulting composition is compressed into 240 mgm-tablets in a conventional tablet making machine. Each tablet contains 50 mgm of the benzylamine salt and is an oral dosage unit composition with effective anti-ulcerogenic action.

EXAMPLE 110

Coated pills

The pill core composition is compounded from the following ingredients:

| | | |
|---|---:|---|
| 3,5-Dibromo-2-hydroxy-N-(trans-4-hydroxy cyclohexyl)-benzylamine hydrochloride | 30.0 | parts |
| Sec. calcium phosphate, anhydrous | 100.0 | parts |
| Colloidal silicic acid | 10.0 | parts |
| Corn starch | 20.0 | parts |
| Polyvinylpyrrolidone | 5.0 | parts |
| Potato starch | 10.0 | parts |
| Maleic acid | 3.0 | parts |
| Magnesium stearate | 2.0 | parts |
| Total | 180.0 | parts |

Preparation:

The ingredients are compounded as described in Example 109, and the composition is compressed into 180 mgm-pill cores which are subsequently coated with a thin shell consisting essentially of a mixture of sugar and talcum. Each coated pill contains 30 mgm of the benzylamine salt and is an oral dosage unit composition with effective anti-ulcerogenic action.

EXAMPLE 111

Gelatin capsules

The capsule filler composition is compounded from the following ingredients:

| | | |
|---|---:|---|
| N-Ethyl-N-cyclohexyl-3,5-dibromo-2-hydroxy-benzylamine hydrochloride | 50.0 | parts |
| Potato starch | 40.0 | parts |
| Talcum | 10.0 | parts |
| Total | 100.0 | parts |

Preparation:

The ingredients are intimately admixed with each other, and 100 mgm-portions of the mixture are filled into gelatin capsules of suitable size. Each capsule contains 50 mgm of the benzylamine salt and is an oral dosage unit composition with effective anti-ulcerogenic action.

EXAMPLE 112

Solution

The solution is compounded from the following ingredients:

| | | |
|---|---:|---|
| 3,5-Dibromo-4-hydroxy-N-(cis-3-hydroxy-cyclohexyl)-benzylamine hydrochloride | 0.5 | parts |
| Sugar | 70.0 | parts |
| Tartaric acid | 0.3 | parts |
| Sec. sodium phosphate . 2 H$_2$O | 1.2 | parts |
| Saccharin sodium | 0.2 | parts |
| Methyl p-hydroxy-benzoate | 0.07 | parts |
| Propyl p-hydroxy-benzoate | 0.03 | parts |
| Essence of eucalyptus-menthol | 0.2 | parts |
| Raspberry flavoring | 0.02 | parts |
| Ethanol, pure | 2.0 | parts |
| Distilled water q.s.ad | 100.0 | parts by vol |

Preparation:

About 50 ml of distilled water are heated to 80° C, and the p-hydroxybenzoates, the sugar, the saccharin sodium, the tartaric acid, the secondary sodium phosphate and the benzylamine salt are dissolved therein. Then, a solution of the essence of eucalyptus-menthol and the raspberry flavoring in the ethanol is stirred in. Subsequently the solution is diluted with distilled water to the indicated volume and filtered until clear. 10 ml of the solution contain 50 mgm of the benzylamine salt and are an oral dosage unit composition with effective antiulcerogenic action.

Analogous results are obtained when any one of the other benzylamines embraced by formula I or a non-toxic, pharmacologically acceptable acid addition salt thereof is substituted for the particular benzylamine salt in Examples 103 through 112. Likewise, the amount of active ingredient in these illustrative examples may be varied to achieve the respective dosage unit ranges set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A secretolytic pharmaceutical dosage unit composition consisting essentially of an inert pharmaceutical carrier and an effective secretolytic amount of a compound of the formula

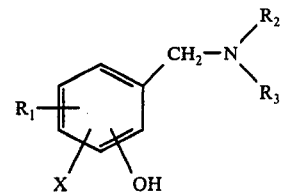

wherein
X is chlorine or bromine;
$R_1$ is hydrogen, chlorine or bromine;
$R_2$ is isopropyl; tert.butyl; tert.pentyl; mono-, di or tri-hydroxy-substituted branched alkyl of 3 to 5 carbon atoms; cyclohexyl; or hydroxycyclohexyl; and
$R_3$ is alkyl of 1 to 4 carbon atoms or, when $R_2$ is other than cyclohexyl, also hydrogen;
or a non-toxic, pharmacologically acceptable acid addition salt thereof.

2. The method of stimulating the secretion of respiratory fluids in a warm-blooded animal, which comprises perorally, parenterally or rectally administering to said animal an effective secretolytic amount of a compound of the formula

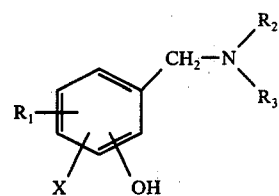

wherein
X is chlorine or bromine;
$R_1$ is hydrogen, chlorine or bromine;
$R_2$ is isopropyl; tert.butyl; tert.pentyl; mono-, di- or tri-hydroxy-substituted branched alkyl of 3 to 5 carbon atoms; cyclohexyl; or hydroxycyclohexyl; and
$R_3$ is alkyl of 1 to 4 carbon atoms or, when $R_2$ is other than cyclohexyl, also hydrogen; or a non-toxic, pharmacologically acceptable acid addition salt thereof.

* * * * *

UNITED STATES PATENT OFFICE
CERTIFICATE OF CORRECTION

Patent No. 4,073,942      Dated February 14, 1978

Inventor(s) JOHANNES KECK et al

It is certified that error appears in the above-identified patent and that said Letters Patent are hereby corrected as shown below:

Col. 10, line 55 - that portion of the formula which now reads

" " 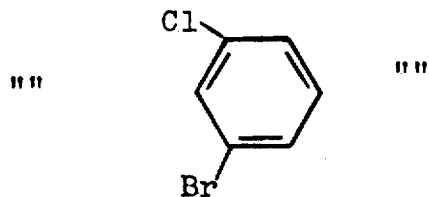 " "

should read

-- 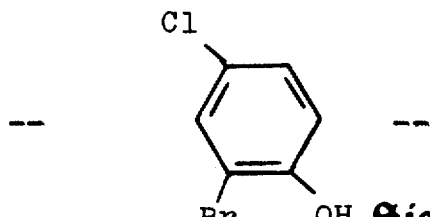 --

Signed and Sealed this

Sixth Day of June 1978

[SEAL]

Attest:

RUTH C. MASON
*Attesting Officer*

DONALD W. BANNER
*Commissioner of Patents and Trademarks*